(12) United States Patent
Breyne et al.

(10) Patent No.: US 6,291,561 B1
(45) Date of Patent: Sep. 18, 2001

(54) PHOTOCHROMIC COMPOSITIONS, PHOTOCHROMIC COMPOUNDS (CO) POLYMER MATRICES

(75) Inventors: Olivier Breyne; You-Ping Chan, both of Lyons; David Henry, Morigny-Champigny; Xavier Lafosse, Gif-sur-Yvette, all of (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/403,827

(22) PCT Filed: May 1, 1998

(86) PCT No.: PCT/US98/09073

§ 371 Date: Feb. 14, 2000

§ 102(e) Date: Feb. 14, 2000

(87) PCT Pub. No.: WO98/50807

PCT Pub. Date: Nov. 12, 1998

Related U.S. Application Data

(60) Provisional application No. 60/050,812, filed on Jun. 26, 1997.

(51) Int. Cl.[7] .............................. C08K 5/35; G02B 5/23; C07D 311/92; C07D 413/00

(52) U.S. Cl. .............................. 524/96; 524/99; 524/110; 523/106; 252/586

(58) Field of Search ............................ 252/586; 523/106; 524/96, 99, 110; 544/150; 549/389

(56) References Cited

U.S. PATENT DOCUMENTS 5,623,005    4/1997    Rickwood et al. .................... 524/96

FOREIGN PATENT DOCUMENTS

98/04937    2/1998    (WO) .

*Primary Examiner*—Kriellion Sanders
(74) *Attorney, Agent, or Firm*—Angela N. Nwaneri; Peter Rogalskyj

(57) ABSTRACT

The object of the present invention is a photochromic composition incorporating:

+ 2-(p-dimethylaminophenyl)2-(p-methoxyphenyl)-5-methyl-7,9-dimethoxy-[2H]-naphtho[1,2-b]pyran (compound (I)), and + 3-(p-methoxyphenyl)-3-phenyl-6-morpholino-3H-naphtho-[2,1-b]pyran (compound (II)).

The invention also relates to said compounds (I) and (II) per se, (co)polymer matrices containing same, advantageously in a mixture, as well as finished products constituted wholly or in part of such matrices and/or containing one and/or the other of said compounds (I) and (II).

28 Claims, No Drawings

PHOTOCHROMIC COMPOSITIONS, PHOTOCHROMIC COMPOUNDS (CO) POLYMER MATRICES

This application is a 371 of PCT/US98/09073 filed May 1, 1998 and which claims benefit of U.S. Provisional Application No. 60/050,812 filed Jun. 26, 1997.

The object of the present invention is to produce particularly efficient photochromic compositions which incorporate two photochromic compounds within its matrix. The invention involves using the two photochromic compounds jointly. The invention is based on a double selection insofar as the two photochromic compounds were selected on the one hand for their intrinsic properties and on the other, for their mutual compatibility and their complementarity (in respect of the tint obtained).

The present invention finally relates to (co)polymer matrices which incorporate one or the other, advantageously both photochromic compounds as well as finished products—glazings, optical device, ophthalmic or solar article etc., constituted wholly or in part of such matrices.

The photochromic compounds are capable of changing color under the influence of a poly- or mono-chromatic light (UV for example) and of returning to their initial color when the luminous irradiation ceases, or under the influence of temperature and/or poly- or mono-chromatic light different from the first.

The photochromic compounds find applications in various fields, for example, for the manufacture of ophthalmic lenses, contact lenses, solar protection glasses, filters, camera optics or photographic apparatus optics or other optical devices and observation devices, glazings, decorative objects, bill elements or even for information storage by optical inscription (coding).

In the field of ophthalmic optics, and in particular the spectacles trade, a photochromic lens which comprises one or more photochromic compounds must have:

a high transmission in the absence of ultraviolets, a low transmission (high colorability) under solar irradiation, adapted coloration and discoloration kinetics, a tint acceptable to the consumer (gray or brown preferably) with a maintenance of the chosen tint during the coloration and the discoloration of the lens, a maintenance of the performances, the properties, within a temperature range of 0°–40° C., a significant durability, since these objectives sought are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a gray or brown tint—tints acceptable to the consumer—necessitates the use in practice of at least two photochromes of different colors, i. e. having distinct maximal absorption wavelengths in the visible. This association further imposes other requirements of the photochromic compounds. In particular, the coloration and discoloration kinetics of the (two or more) associated active photochromic compounds must be essentially identical. It goes without saying for their stability with time and also for their compatibility with a plastic or inorganic support.

Amongst the numerous photochromic compounds described in the prior art, benzopyrans and naphthopyrans may be cited which are described in patents U.S. Pat. Nos. 3,567,605, 3,627,690, 4,818,096, 4,826,977, 5,200,116, 5,238,981, 5,458,814, WO 96/04576 and in the Research Disclosure No. 36144, which are of the formula below:

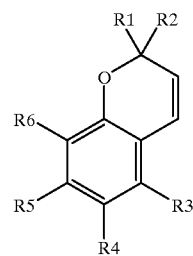

These compounds claim to satisfy the specifications defined above. In reality, if these compounds really do have one or more of the basic properties sought, such as a high transmission in the absence of ultraviolets and a high colorability under solar irradiation, none of them have the complete combination of the properties sought which are necessary for the production of satisfactory articles which may be manufactured industrially.

The Applicant, confronted with the specifications proposes a novel solution which is based on a double selection.

It is in fact to the credit of the Applicant to have selected on the one hand a photochromic compound (compound (I) of the invention which exhibits a violet color) amongst the compounds described in its patent application FR 96 09384, which has not yet been published, and on the other hand, a photochromic compound (compound (II) of the invention which exhibits a yellow color) amongst the compounds described in the application WO-A-94 22850; compounds ((I) and (II)), both efficient per se, and whose association, in addition, has revealed to be particularly interesting insofar as the two compounds, which are perfectly compatible, are complementary in exhibiting a gray tint (acceptable to the consumer).

Thus, according to its first object, the invention relates to a photochromic composition incorporating 2-(p-dimethylaminophenyl)-2-(p-methoxyphenyl)-5-methyl-7,9-dimethoxy-[2H]-naphtho[1,2-b]pyran (compound (I)), and 3-(p-methoxyphenyl)-3-phenyl-6-morpholino-3H-naphtho-[2,1-b]pyran (compound (II)).

The photochromic composition advantageously contains compounds (I) and (II) in a compound (I)/compound (II) weight ratio between 7 and 10 (more advantageously still between 8 and 9). The best results of the exhibition of the gray tint are within the context of this advantageous variant.

According to its first object, the present invention therefore relates to the joint use of 2-(p-dimethylaminophenyl)-2-(p-methoxyphenyl)-5-methyl-7,9-dimethoxy-[2H]-naphtho[1,2-b]pyran (compound (I)) and 3-(p-methoxyphenyl)-3-phenyl-6-morpholino-3H-naphtho-[2,1-b]pyran (compound (II)) as photochromic agents; the two photochromic agents being advantageously used in a compound (I)/compound (II) weight ratio between 7 and 10 (more advantageously still between 8 and 9). Such a joint use is generally made within a polymeric matrix to which it is desired to confer photochromic properties.

Such a joint use has revealed to be particularly interesting insofar as the photochromic compounds (compound (I) and compound (II)) each have interesting photochromic properties which are compatible (notably from a kinetics and thermal point of view) and complementary with the color (see Examples below).

Compounds (I) and (II) of the photochromic compositions of the invention are now described below in detail. The formula developed for each one of them as well as a means of synthesis of same appear in the Example section of the present text. These compounds are presently claimed.

Compound (I) of the invention consists of 2-(p-dimethylaminophenyl)-2-(p-methoxyphenyl)-5-methyl-7,9-dimethoxy-[2H]-naphtho[1,2-b]pyran.

It is of the general formula of the photochromic naphthopyrans described by the Applicant in its application FR 96 09384 of the Jul. 25, 1996; general formula:

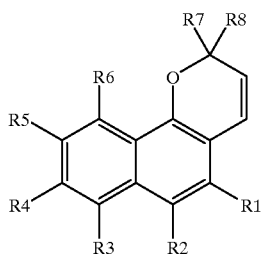

in which at least two of the substituents $R_3$ to $R_6$ (advantageously $R_3$ and $R_5$) are C1 to C6 alkoxy groups (advantageously methoxy groups). In application FR 96 09384, $R_7$ and $R_8$ are described in a very broad manner, notably as aromatic or polyaromatic groups optionally substituted with at least one C1 to C5 alkoxy, C1 to C5 alkyl, C2 to C12 amine, C6 to C12 aryl, or $CF_3$ group. In application FR 96 09384, a conventional synthetic route to naphthopyrans is further described:condensation of an appropriately substituted 1-naphthol derivative (substituents $R_1$ to $R_6$) and a propargylic alcohol derivative (substituents $R_7$ and $R_8$).

Within the context of the present invention, the Applicant has selected compound (I)—a violet molecule—of the general formula above in which:

.$R_1$=$CH_3$

.$R_2$=$R_4$=$R_6$=H

.$R_3$=$R_5$=$OCH_3$

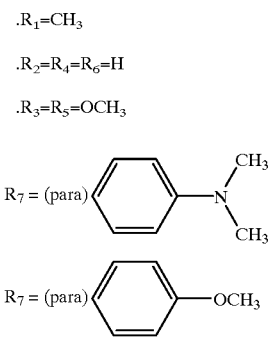

Surprisingly, the compound has very interesting photochromic properties which are superior to those of its homologues; and has notably:

a weak initial coloration, a strong colorability with two absorption bands in the visible (see the Table below: λmax 1, λmax 2), discoloration kinetics adapted (to the application sought), a low thermal dependence.

The Applicant has notably evaluated the properties in an original matrix which is specified further on in the present text. The matrix is based on a short-chain (meth)acrylate difunctional monomer and a long-chain alkenic difunctional monomer. Used at 0.05% by weight within the matrix (conditioned under 2 mm thickness), the compound has led to the results shown in the Table below.

| Com-pound | λmax 1 | λmax 2 | T0* at 489 nm | T0* at 588 nm | DOin-duced** at 489 nm | DOin-duced** at 588 nm | t½*** |
|---|---|---|---|---|---|---|---|
| I | 489 nm | 588 nm | 85% | 86% | 0.58 | 0.94 | 127 s |

*T0: transmission before exposure.
**DOinduced = $DO_\infty$ – $DO_0$ wherein $DO_0$ is the optical density before exposure and $DO_\infty$ the optical density after exposure under a xenon lamp (40,000 lux).
***t½ half-time of fading (expressed in seconds). This parameter characterizes the kinetics of return to the initial state. After 15 minutes' exposure under the above conditions ($DO_{15}$), the exposure is cut off and the time necessary for a return to $\frac{DO_{15} - DO_0}{2}$ is timed; this is $t_{1/2}$.

Upon considering the results, the person skilled in the art grasps straight away the beneficial advantages of compound (I) selected from amongst the numerous naphthopyrans of the application FR 96 09384. Compound (I) must nonetheless be associated with a complementary yellow photochrome in order to provide a gray tint.

Compound (II) of the invention consists of 3-(p-methoxyphenyl)-3-phenyl-6-morpholino-3H-naphtho-[2,1-b]pyran. It is of the general formula of the photochromic naphthopyrans described in the application WO-A-94 22850; general formula:

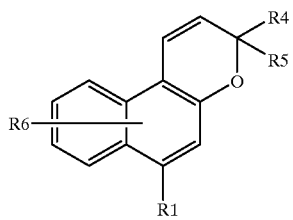

in which:

$R_1$ represents an amine group (advantageously morpholino or piperidino);

$R_4$ and $R_5$ independently represent an alkyl, an alkenyl, a heterocyclic or carbocyclic group (advantageously, a phenyl, p-methoxyphenyl or trifluoromethylphenyl) or are bound in order to represent a ring or a hetrocyclic ring;

$R_6$ represents a hydrogen or a substituent.

Naphthopyrans characteristically have a substituted amino group in position 6 (substituent $R_1$). They are obtained by a synthetic route analogous to that indicated above with reference to the compounds described in the application FR 96 09384: condensation of an appropriately substituted 2-naphthol derivative (substituents $R_1$ and $R_6$) and a propargylic alcohol derivative (substituents $R_4$ and $R_5$).

Within the context of the present invention, the Applicant has selected compound (II)—a yellow molecule—of the above formula in which:

.$R_1$=morpholino

.$R_4$=phenyl

.$R_5$=p-methoxyphenyl

.$R_6$=H.

Compound (II) is superior to its homologues insofar as a compromise in terms:
of weak initial coloration,
of high colorability,
of discoloration kinetics, and
of thermal dependence
is obtained along with it.

This affirmation is corroborated by the results given in the Table below.

Compounds C1, C2, C3, other naphthopyrans according to the application WO-A-94 22850, are identified by their developed formula in the Example part of the text. All compounds (II), C1, C2, C3 were tested under the same conditions as those indicated above with reference to compound (I).

| Compound | λmax (nm) | T0 (%) | DO induced | $t_{1/2}$ (s) |
|---|---|---|---|---|
| II | 439 | 79 | 1.65 | 88 |
| C1 | 456 | 74 | 1.37 | 52 |
| C2 | 430 | 68 | 1.60 | 150 |
| C3 | 430 | 79 | 1.77 | 164 |

Compound (II) furthermore reveals to constitute a partner of choice for compound (I), in a way as to express a tint acceptable to the consumer, i. e. gray, under favorable conditions (of initial color, of interesting colorability, of adapted discoloration and of acceptable thermal dependence).

Compound (II) has in fact the specifications which determine the profile of an efficient partner of compound (I). The Applicant, after analyzing the spectral curve of compound (I) had established such specifications. It is summarized in the Table below:

| λmax (nm) | T0 (%) | DO induced | $t_{1/2}$ (s) |
|---|---|---|---|
| 435–450 | >77 | >1.50 | <127 |

The Applicant has therefore, within the context of the present invention, selected two compatible efficient photochromic compounds which are claimed either individually or in a mixture.

It is hereby indicated that in general, the photochromic composition of the invention only contains the two compounds in a weight ratio which is optimized in order to obtain a gray tint sought-after. However, it is in no way excluded from the context of the present invention that the composition contains at least one other obviously compatible, photochromic compound.

The compounds of the invention and their mixtures ((I), (II), (I)+(II)) may be dispersed uniformly in the mass or on the surface of a polymer matrix. The most interesting applications of the compounds of the invention are in fact those in which the photochrome(s) is (are) uniformly dispersed within or on the surface of a polymer, a copolymer or a mixture of polymers. The (co)polymer matrix which comprises the photochromes of the invention (compound (I), compound (II)) and advantageously the mixture of photochromes of the invention constitutes another object of the present invention.

The implementation methods envisagable for obtaining such a matrix are very varied. Amongst those known to the person skilled in the art, diffusion in the (co)polymer from a suspension or solution of photochrome(s), in a silicone oil, in an aliphatic or aromatic hydrocarbon, in a glycol, or from another polymer matrix, may be cited for example. The diffusion is commonly effected at a temperature of 50° to 200° C. for a period of time of 15 minutes to several hours, according to the nature of the polymer matrix. Another implementation technique consists in mixing the photochrome(s) in a formulation of polymerizable materials, in depositing this mixture on a surface or in a mold and in then carrying out the copolymerization. These and other implementation techniques are described in the article by Crano et al. "Spiroxazines and their use in photochromic lenses" published in Applied Photochromic Polymer Systems, Ed. Blackie and Son Ltd—1992.

The following products ((co)polymers) may be mentioned as examples of preferred polymer materials for optical applications of the photochromic compounds of the invention, taken alone or in a mixture:

a) optionally halogenated alkyl, cycloalkyl, aryl or aralkyl mono-, di-, tri- or tetraacrylate or mono-, di-, tri- or tetramethacrylate or having at least one ether and/or ester and/or carbonate and/or carbamate and/or thiocarbamate and/or urea and/or amide group, b) polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymer, cellulose acetate, tricellulose acetate, cellulose acetate-propionate or polyvinylbutyral, c) copolymers of two or more types of monomer or mixtures of polymers mentioned above, d) copolymers obtained by radical polymerization of a composition comprising a mixture of at least one or more difunctional monomers of type (a) and one or more difunctional monomers of type (b):
the difunctional monomer(s) of type (a) having one or the other of the formulae (A) and (A') below:
formula (A):

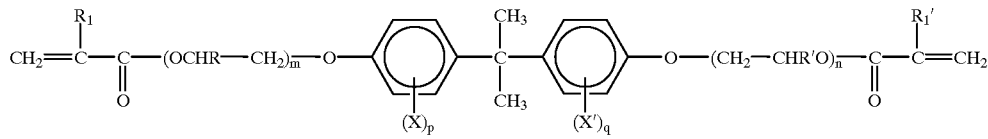

in which:

$R_1$, $R'_1$, R and R', identical or different, independently are a hydrogen or a methyl group;

m and n are, independently, integers between 0 and 4 inclusive; and are advantageously independently equal to 1 or 2;

X and X', identical or different, are a halogen and preferably represent chlorine and/or bromine;

p and q are, independently, integers between 0 and 4 inclusive;

formula (A'):

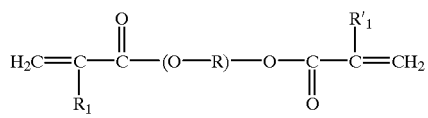

in which:
R$_1$ and R'$_1$, identical or different, independently are a hydrogen or a methyl group;
R is a linear or branched alkyl radical having from 2 to 8 carbon atoms, a cycloalkyl radical having from 3 to 6 carbon atoms, an ether radical of formula (R'—O—R") in which R' and R", identical or different, independently are a linear or branched alkyl radical having from 2 to 4 carbon atoms;
the difunctional monomer(s) of type (b)—long chain alkenic difunctional oligomer—being of one or the other of formulae (B), (B') and (B") below:
formula (B):

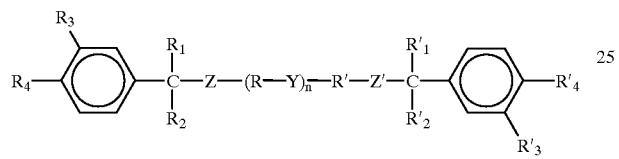

in which:
R$_1$, R'$_1$, R$_2$ and R'$_2$, identical or different, independently are hydrogen or a linear or branched alkyl radical, advantageously linear, having from 1 to 4 carbon atoms; and correspond particularly advantageously to a methyl group;
R$_3$ and R$_4$, different, are independently one hydrogen and the other an alkenyl radical having from 2 to 6 carbon atoms, advantageously from 2 to 4 carbon atoms and particularly advantageously an isopropenyl radical;
R'$_3$ and R'$_4$, different, are independently one hydrogen and the other an alkenyl radical having from 2 to 6 carbon atoms, advantageously from 2 to 4 carbon atoms and particularly advantageously an isopropenyl radical;
Z represents a carbamate function (—NH—CO—O—), a thiocarbamate function (—NH—CO—S—) or a urea function (—NH—CO—NH—);
Z', independent from Z and advantageously respectively with respect to Z, represents a carbamate function (—O—CO—NH—), a thiocarbamate function (—S—CO—NH—) or a urea function (—NH—CO—NH—);
R' represents a linear or branched alkyl radical having from 2 to 4 carbon atoms;
R, identical or different when n≧2, is a linear or branched alkyl radical having from 2 to 4 carbon atoms;
Y, identical or different when n≧2, is oxygen or sulfur;
n is an integer defined in such a way that the total number of carbon atoms contained in the long chain situated between the two motifs Z and Z' is at least equal to 18 and is advantageously between 18 and 112 inclusive;
formula (B'):

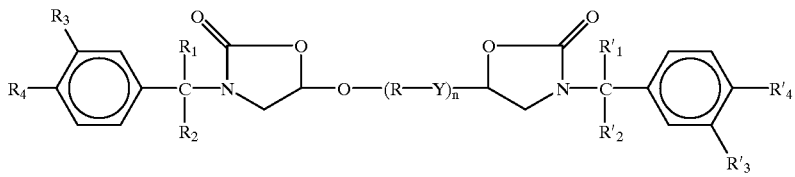

in which:
R$_1$, R$_2$, R$_3$, R$_4$, R'$_1$, R'$_2$, R'$_3$, R'$_4$, R and Y are such as defined above with reference to formula (B);
n is an integer defined in such a way that the total number of carbon atoms contained in the long chain of the motif (R—Y)$_n$ is at least equal to 22 and is advantageously between 22 and 104 inclusive;
formula (B")

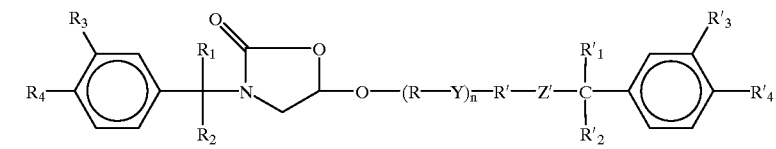

in which:

R$_1$, R$_2$, R$_3$, R$_4$, R'$_1$, R'$_2$, R'$_3$, R'$_4$, R, R' and Y are such as defined above with reference to formula (B);

Z' is a carbamate function (—O—CO—NH—) or Z' is a thiocarbamate function (—S—CO—NH—); advantageously Z' is a carbamate function;

n is an integer defined in such a way that the total number of carbon atoms contained in the long chain of the motif (R—Y)$_n$—R' is at least equal to 22 and is advantageously between 22 and 104 inclusive.

It is most particularly recommended to bring in the compounds of the invention (advantageously in a mixture) in a matrix of type d) above. Such a matrix exhibits good optical properties. Within it, the photochromic compounds of the invention rapidly and at best express their excellent photochromic properties. Such a matrix is obtained by radical polymerization of at least one long-chain alkenic difunctional monomer with at least one short-chain (meth) acrylic difunctional monomer. The resulting matrix has then a nanophasic structure which provides it with interesting properties. In fact, the short-chain (meth)acrylic difunctional monomer(s) (of type (a) and of formula (A), (A')) bring about rigidity, this rigidity being modulated by the presence of the long-chain alkenic difunctional monomer(s) (of type (b) and of formula (B), (B'), (B")) which, in a surprising way, also enable providing the composition with excellent photochromic properties. Thus, the difference in functionality of the monomers of type (a) and (b) advantageously retards the gelling of the resulting polymerizable composition. Such a matrix is claimed by the Applicant in a parallel application The nature and the advantageous variants of it are specified below.

It is possible for the polymerisable composition from which it is obtained to contain, in addition to the difunctional monomers of type (a) and (b):

(c) at least one aromatic monovinylic monomer of formula (C):

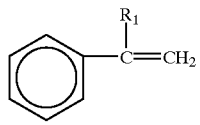

in which R$_1$=H or CH$_3$; the monovinylic monomer advantageously consisting of styrene;
and/or (d) at least one aromatic divinylic monomer of formula (D):

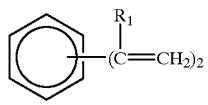

in which R$_1$=H or CH$_3$; the divinylic monomer advantageously consisting of divinylbenzene;
and/or (e) at least one (meth)acrylic monomer of formula (E):

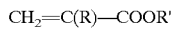

CH$_2$=C(R)—COOR' in which R=H or CH$_3$ and R' is a linear or branched alkyl radical having from 4 to 16 carbon atoms, an optionally substituted (generally by a C$_1$–C$_6$ alkyl group) methylphenyl or methylphenoxy radical or a polyoxyethoxyl group of formula —(CH$_2$—CH$_2$—O)$_n$R" in which n is an integer between 1 and 10 and R"=CH$_3$ or C$_2$H$_5$; the (meth)acrylic monomer advantageously consisting of ethylhexylmethacrylate;
and/or (f) diallylphthalate.

The polymerizable composition generally contains an effective amount of at least one radical polymerization initiator as well, and an effective amount of at least one polymerization modifier, the polymerization modifier being preferably a chain transfer agent.

The natures and the amounts of each one of the intervening compounds or those which can intervene in the polymerizable compositions of the invention, and notably in the preferred compositions of the invention, which generate the matrices of type (d) by copolymerization within which matrices the photochromic compounds of the invention (compound (I) and/or (II)) advantageously intervene shall now be examined in greater detail.

The monomers of type (a) of formula (A) and (A') constitute the short-chain difunctional (meth)acrylate monomers (i.e. diacrylates, dimethacrylates or mixed: acrylates-methacrylates) of the polymerizable composition(s) of the invention. The monomers may or may not have a pronounced symmetry (R/R', R$_1$/R'$_1$, X/X'). They enable conferring the rigidity, and therefore the mechanical properties, to the polymer (to the resin or matrix) obtained from the polymerizable composition.

The monomers of type (a) may or may not all be of the same formula (A) or (A') . . . Thus the polymerisable compositions, precursors of the preferred matrices contain:

either monomers of a same formula (A) (at least one);
or monomers of a same formula (A') (at least one);
or mixtures (non mixed) of monomers of different formulae (A);
or mixtures (non mixed) of monomers of different formulae (A');
or mixtures (mixed) of monomers of formula(e) (A) and of formula(e) (A').

According to a preferred variant of the invention, one or more symmetrical monomers of type (a) are used. As contemplated by the present invention, monomers of type (a), of formula (A) or (A') in which the R$_1$ and R'$_1$ groups are identical, the same as R and R' groups as well as the X and X' substituents for the compounds of formula (A) are deemed to be symmetrical.

The symmetrical monomers of type (a) of formula (A) are known and are available commercially or are easily accessible to the person skilled in the art. In fact, it may be noted that the monomers which do not have a halogen on the aromatic rings correspond to the first monomers of formula (I) in the sense of the WO-A-92/05209 document. The monomers of type (a) of formula (A) having halogen(s) on the aromatic ring(s) will be easily obtained by the person skilled in the art by using derivatives appropriately substituted on the aromatic ring(s). Within the context of the invention, the monomers of formula (A), in which R and R', identical, are hydrogen or a methyl group, R$_1$ and R'$_1$ are a methyl group, m and n are independently equal to 1 or 2, and p=q=0, are preferred. A particularly advantageous variant corresponds to the monomer of formula (A) of the above type with, in addition, R=R'=H and m=n=2. The monomer is marketed by Akzo Nobel (NL) under the commercial designation DIACRYL 121. The synthesis of the dissymmetrical monomers of formula (A) are of no particular problem to the person skilled in the art.

The monomers (a) of formula (A') are also well-known and result from the conventional reaction of an aliphatic diol or of a short-chain alkyleneglycol (with a maximum of 8 carbon atoms in the chain) with at least one type of (meth) acrylic derivative depending on whether it is desired to obtain monomers of formula (A') which are symmetrical or dissymmetrical at their ends.

These monomers of type (a) intervene generally in the composition to be polymerized at a rate of 40 to 99 parts by weight for 100 parts by weight of the mixture of monomers of type (a) and (b). If they intervene in a smaller amount, the polymerizable composition has a tendency to retract during its polymerization inducing a premature turn-out which, in turn, is responsible for a deterioration of the optical properties of the final resin.

The monomers (b) of formula (B), (B') and (B") constitute the long-chain difunctional alkenic monomers of the polymerizable composition of the invention. The monomers have or have not a more or less pronounced symmetry ($R_1/R'_1$, $R_2/R'_2$, $R_3/R'_3$, $R_4/R'_4$, Z/Z').

These monomers of type (b) may or may not all have the same formula (B), (B') or (B") . . . Thus, the invention comprises as well the polymerizable compositions which contain:

either monomers of a same formula (B) (at least one);

or monomers of a same formula (B') (at least one);

or monomers of a same formula (B") (at least one);

or mixtures (non mixed) of monomers of different formulae (B);

or mixtures (non mixed) of monomers of different formulae (B');

or mixtures (non mixed) of monomers of different formulae (B");

or mixtures (mixed, binary or ternary) of monomers selected from the monomers of formula(e) (B), of formula(e) (B') and of formula(e) (B").

The presence of monomer(s) of type (b) in the polymerizable composition of the invention allows a softening of the polymer network by loosening the network without lowering for as much the degree of cross-linking of the polymer. This allows conferring interesting mechanical properties to the material at high temperature, characterized notably by a high elasticity modulus value at the rubbery "plateau" of the polymer.

The monomers of type (b) which are long-chain alkenic difunctional oligomers, the chain being a polyoxyalkylene or polymercaptoalkylene chain, even a mixed chain, are obtained according to the conventional conditions of organic synthesis by the reaction:

between one or several derivatives having a functionality of the alkenylisocyanate type, of formula I and/or II:

formula I

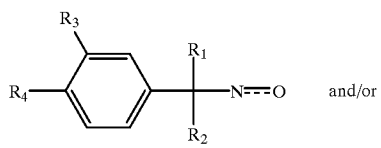

and/or formula II

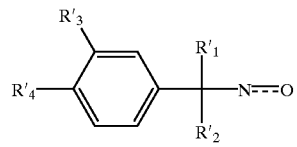

in which $R_1$, $R_2$, $R_3$, $R_4$, $R'_1$, $R'_2$, $R'_3$ and $R'_4$ are such as defined above. According to a preferred variant of the invention, the monomers of type (b) used are symmetrical at their ends. In order to do this, a single type of alkenylisocyanate derivative (thus formulae I and II are identical) is used. In a particularly advantageous way, a vinylisocyanate derivative is used in which $R_1=R_2=CH_3$ (or $R'_1=R'_2=CH_3$), $R_3$ (or R'3) is an isopropenyl radical and $R_4$ (or $R'_4$) is hydrogen, thus corresponding to the 3-isopropenyl-α,α-dimethylbenzylisocyanate (of general designation m-TMI® defined above). The oligomers (b) obtained from the derivatives are preferred;

and a compound which intrinsically has a long chain, the compound being:

either a compound which is symmetrical about its terminal functions which correspond:

to a diol of formula $HO—(R—Y)_n—R'—OH$;

or to a dithiol of formula $HS—(R—Y)_n—R'—SH$;

or to a diamine of formula $H_2N—(R—Y)_n—R'—NH_2$; which allows obtaining the intrinsically symmetrical oligomers of formula (B) (intrinsically symmetrical means monomers of formula (B) in which the Z and Z' groups are functions of identical nature);

or to a biepoxy of formula

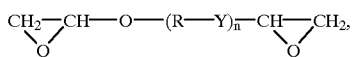

the reaction thus leading to the synthesis of the oligomers of formula (B');

or a compound which is dissymmetrical about its terminal functions:

it being possible for the functions to be an alcohol, thiol or amine function; all combinations being possible: these compounds enabling obtaining other intrinsically dissymmetric difunctional oligomers of formula (B) (intrinsically dissymmetrical means monomers of formula (B) in which the Z and Z' groups are functions of different nature);

the functions respectively being an epoxy function and an alcohol function or an epoxy function and a thiol function, the compounds then being of formula

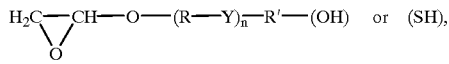

the reaction thus leading to the synthesis of the oligomers of formula (B").

In every case, R, R', Y and n are such as defined above; preferentially, Y is oxygen (the long chain then being a polyoxyalkylene chain).

The molecular mass of the long polyoxyalkylene and/or polymercaptoalkylene chain which correspond to the $(R—Y)_n—R'$ or $(R—Y)_n$ radical in formulae (B, B', B") specified above, is generally at least equal to 500 g.mol$^{-1}$ and lower than 2000 g.mol$^{-1}$; and preferably, the molecular mass is between 600 g.mol$^{-1}$ and 900 g.mol$^{-1}$.

In a particularly advantageous way, one or several intrinsically symmetrical monomers of type (b) of formula (B) (as defined above) are brought to intervene:

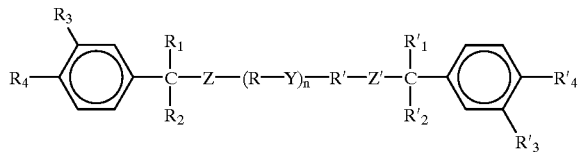

in which R, R', $R_1$, $R_2$, $R_3$, $R_4$, $R'_1$, $R'_2$, $R'_3$, $R'_4$ and Y are such as defined above (and advantageously so that the two end of the molecule are identical; i e.: $R_1=R'_1$, $R_2=R'_2$, $R_3=R'_3$ and $R_4=R'_4$, with even more advantageously $R_1=R'_1=R_2=R'_2=CH_3$ and $R_3=R'_3$ and $R_4=R'_4$ with one of $R_3$ and $R_4$ being hydrogen and the other being an isopropenyl group) and Y is such as defined above and advantageously consists of an oxygen (X=O) and:

(α) Z and Z' are carbamate functions of formula (—NH—CO—O—) and (—O—CO—NH—) respectively;

n is an integer defined in such a way that the total number of carbon atoms contained in the long chain situated between the two motifs Z and Z', is between 18 and 112; and advantageously, in the case of a polyoxyalkylene chain, is between 24 and 112 and particularly advantageously between 26 and 50 in the case of a polyoxyalkylene of molecular mass between 600 and 900 g.mol$^{-1}$;

or (β) Z and Z' are thiocarbamate functions of formula (—NH—CO—S—) and (—S—CO—NH—) respectively n is an integer defined in such a way that the total number of carbon atoms contained in the long chain situated between the two motifs Z and Z', is between 18 and 108; and advantageously, in the case of a polyoxyalkylene chain, is between 24 and 108 and particularly advantageously between 28 and 46 in the case of a polyoxyalkylene chain of molecular mass between 600 and 900 g.mol$^{-1}$;

or (γ) Z and Z' are urea functions (—NH—CO—NH—)

n is an integer defined in such a way that the total number of carbon atoms contained in the long chain situated between the two motifs Z and Z', is between 18 and 112; and advantageously, in the case of a polyoxyalkylene chain, is between 24 and 112, and particularly advantageously between 28 and 50 in the case of a polyoxyalkylene of molecular mass between 600 and 900 g.mol$^{-1}$.

The person skilled in the art will have understood that formula (B), in the case (α) above wherein the number of carbon atoms contained in the long chain is equal to 50, may for example be written:

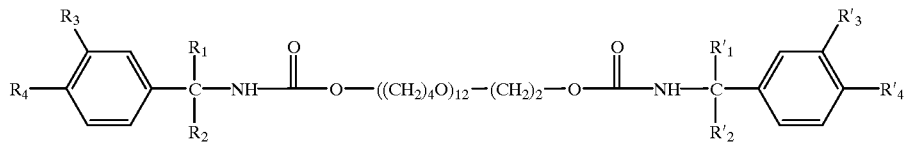

In the same way, the person skilled in the art will have understood that generally the minimal values mentioned above which define the number of carbon atoms in the long chain of motif (R—Y)$_n$—R' or (R—Y)$_n$, correspond to compounds having a polymercaptoalkylene chain (Y=S).

In a particularly advantageous manner, the monomer(s) of type (b) have a general formula (B) such as defined above in which:

$R_1$, $R_2$, $R'_1$ and $R'_2$, identical, are methyl radicals; $R_3$ and $R'_3$ are an isopropenyl radical; $R_4$ and $R'_4$ are hydrogen and either Z and Z' are urea functions (—NH—CO—NH—) and R' represents an ethylene or propylene group;

n is an integer equal to 13 or 19 which defines a total number of carbon atoms between Z and Z' equal to 28 or 40 when (R—Y)$_n$ is a polyoxyethylene chain; or n is an integer equal to 10 or 14 which defines a total number of carbon atoms between Z and Z' equal to 33 or 45 when (R—Y)$_n$ is a polyoxypropylene chain; or n is an integer between the lower limit values (10 to 13) and upper limit values (14 to 19) such as defined above, when (R—Y)$_n$ is a polyoxyethylene/polyoxypropylene mixed chain;

or Z and Z' are carbamate functions of formulae (—NH—CO—O—) and (—O—CO—NH—) respectively, and R' represents an ethylene group;

(R—Y)$_n$ represents a long polyoxyethylene chain;

n is an integer equal to 13 or 19 which defines the total number of carbon atoms contained in the long chain situated between the two motifs Z and Z' equal to 28 or 40.

The monomers of type (b) generally intervene in the composition to be polymerized at a rate of 1 to 60 parts by weight for 100 parts by weight of the mixture of monomers of type (a) and (b).

The polymerizable composition may furthermore contain, as already indicated, other monomers. Generally, for 100 parts by weight of the mixture of monomers of type (a) and (b), the composition can contain from 1 to 60 parts by weight (advantageously from 10 to 50 parts by weight) of at least one monomer selected from the alkenic monomers (such as those of formulae (C) and (D) and diallylphthalate (f)), advantageously vinylic and allylic, (meth)acrylic monomers (such as those of formula (E)) and mixtures thereof. In light of the effects sought-after, when these types of monomer are added, the person skilled in the art will know to determine and optimize the intervening amounts of each type of the monomer (in any case, the total amount of the monomer(s) which intervene in the polymerizable composition is between 1 to 60 parts by weight of the mixture of monomers of type (a) and (b)).

The vinylic monomers of formula (C)—styrene and/or methylstyrene—intervene in combination with the monomer (s) of type (a) in order to loosen the network. The intervention of styrene may be particularly advantageous insofar as this polymerized compound has a rather high refractive index (n=1.595). Styrene constitutes the particularly preferred compound of this class of monomer.

The compound of formula (D) consists of divinylbenzene (DVB) or di(methylvinyl)benzene. Divinylbenzene is the particularly preferred compound of formula (D). The intervention of at least one compound of formula (D) may reveal to be advantageous in that notably the compound moderates, in a general manner, the effects of the compound(s) of formula (C). The beneficial action of such a compound of formula (D) has been notably demonstrated on the expression of photochromic properties. With reference to divinylbenzene, insofar as this polymerized compound has a relatively high refractive index (n=1.61), its intervention is also beneficial in that it leads to an increase in the refractive index of the polymers of the invention.

The polymerizable composition also contains advantageously at least one compound of formula (E). It is a (meth)acrylic monomer such as defined above. It may notably be butyl, pentyl, hexyl, heptyl, octyl or 2-ethylhexyl (meth)acrylate or even ethyltriglycol(meth)acrylate. 2-Ethylhexylmethacrylate (EHMA) is the preferred compound of formula (E). The presence of this type of compound has revealed to be advantageous for the turning-out of the polymerized material and for the implementation of finishing treatments of the latter.

Finally, the polymerizable composition may contain diallylphthalate which notably allows adjusting the index and/or other optical and mechanical properties.

As specified above, the intervention of the compounds of formula (C) and/or (D) and/or (E) and/or diallylphthalate is not obligatory. It does however reveal to be generally advantageous.

The monomers of types (a), (b) and (f) and of formulae (C), (D) and (E) are the principal constituents—insofar as they intervene or can intervene in relatively consequent amounts—of the polymerizable compositions from which copolymers or resins or matrices are generated, within which the photochromic compounds (I) and/or (II) of the invention are made to intervene. The copolymers are obtained from the monomers by a conventional radical copolymerization process. The copolymerization is generally carried out as specified above in the presence of an effective amount of at least one polymerization modifier and at least one radical polymerization initiator.

The polymerization modifier generally intervenes at a maximal rate of 5% by weight, advantageously at the rate of 0.01 to 2% by weight, with respect to the weight of monomers to be copolymerized. It is hereby noted that it is possible to do away with the presence of such a polymerization modifier in the hypothesis where the material is prepared under a reduced thickness (e<2.0 mm). In that situation, the problem associated with the evacuation of heat are not encountered. For the preparation of a resin of the invention having a thickness greater than 2.0 mm, the presence of a polymerization modifier in the amounts indicated above is generally opportune. It is highly advised against going over the maximal content of 5% indicated above since the glass transition temperature of the material prepared becomes too low. It is highly recommended for the preparation of the material (lens) of thickness between 1.5 and 20 mm, a polymerization modifier content of about 0.5 wt. %. It has been noted that the colorability and the darkening kinetics of the matrix increase with the amount of polymerization modifier which intervenes. In the same way, when this amount goes up, the mechanical resistance increases and the optical quality improves.

It is obviously appropriate that the polymerization modifier does not destroy the photochromic coloring agent(s) present during the polymerization and/or do not induce a discoloration of the material on its own. The polymerization modifier is advantageously a chain transfer agent. The chain transfer agent can be a non-halogenated chain transfer agent such as a linear alkane thiol or bis-mercapto-ethyl ether. Dodecanethiol may be cited as an example of a linear alkane thiol without being limiting. It is not excluded to use other types of chain transfer agents such as alkane thiols substituted with at least one aryl or alkyl radical or thiophenols. All these compounds are familiar to the person skilled in the art and are commercially available.

The radical polymerization initiator or intervening catalyst (which can be a thermal initiator, a photoinitiator, or a combination of these), must itself be substantially "inert" towards photochromic coloring agent(s) present. The catalyst is generally used at a rate of 0.001 to 1% by weight, preferably from 0.005 to 0.5% by weight, with respect to the weight of the monomers present.

For thermal polymerization, the initiator may preferably be selected from the diazo compounds. These compounds are familiar to the person skilled in the art and are commercially available. Examples of such diazo compounds are azobisisobutyronitrile (AIBN) and 2,2'-azobis(2-methylbutyronitrile)(AMBN). In the absence of such a catalyst or in the presence of too low an amount of it, it becomes necessary to carry out the copolymerization at a higher temperature and this renders the reaction difficult to control . . . In the presence of too great an amount of catalyst, an excess of free radicals may be generated, this excess of free radicals inducing a destruction of the photochromic coloring agent(s) optionally present and an accelerated fatigue of the final material. In this latter hypothesis, the reaction carried out may also accelerate and become difficult to control.

Another way to polymerize the composition is to use UV or visible light. In this process, the photoinitiator can be selected from molecules known in the field such as described in "Photoinitiators for Pigmented Systems" by K. Dictliker/Radiation curing in Polymer Science and Technology: Vol 2; photoinitiating systems—FOUASSIER J. P., RABECK J. F. Elsevier Applied Science pp 155. Ch3. In this case, as in thermal polymerisation, the photoinitiator must of necessity be substantially "inert" towards photochromic dyes. Examples of useful photoinitiators include benzophenones, thioxanthones, alpha-amino-aceteophenone derivatives, acylphosphine oxides, bisacylphosphine oxides and many other such compounds known to those skilled in the art. Specific examples of such compounds include acylphosphates and acyldibenzoxaphine oxide. Acylphosphine oxides can be used either alone or in combination with other classes of photoinitiators such as alpha-hydroxy ketones and benzyldimethyl ketal. One particularly useful example of a photoinitiator is IRGACURE 819 (from CIBA-GEIGY). The two types of polymerization (thermal and photopolymerization) can be used independently or in any combination to obtain the lens.

An original type of (co)polymer matrix has at length been described above within which the photochromic compounds of the invention therefore advantageously intervene, taken alone or advantageously in a mixture. Together with the photochromic compounds, at least one other photochromic compound, (vide supra), and/or, at least one non photochromic coloring agent, this with the aim of adjusting the gray tint in the darkened state, and/or, one or more stabilizers, such as an anti-oxidant for example, and/or, one or more anti-UV, and/or, one or more anti-radicals, and/or, one or more deactivators of photochromic excited states, may be brought in a manner per se.

These additives may notably allow improving the durability of the intervening photochromic compound(s).

The photochromic compounds of another type, non-photochromic coloring agents, stabilizers, are prior art products known to the person skilled in the art.

According to its last object, the present invention relates to finished products or articles (glazings, notably for buildings, locomotives, automobiles; optical devices; ophthalmic or solar articles, notably lenses; decorative articles; solar protection articles; articles useful for storing information . . . ) which contain an effective quantity of at least one of the photochromic compounds (I) or (II) and advantageously an effective amount of a mixture of the compounds (I) and (II). The articles may notably be constituted, wholly or in part, of a (co)polymer matrix which therefore contains alone or preferably, a mixture of photochromic compounds (I) and (II).

The present invention is illustrated by the following Examples, of synthesis and photochromic validation, of the compounds of the invention.

EXAMPLE 1

Synthesis of Compound (I)

Compound (I) (described in the patent application FR 96 09384) is obtained by heating a mixture of 1-(p-dimethylaminophenyl)-1-phenyl-2-propyn-1-ol and 5,7-dimethoxy-3-methyl-1-naphthol in refluxing tetrahydrofuran in the presence of p-toluenesulfonic acid; the naphthol having been prepared according to the method described in J. Org. Chem. 1986, vol 51, p271–273 (Sibi et al).

EXAMPLE 2

Synthesis of Compound (II)

Compound (II) is synthesized according to the following scheme:

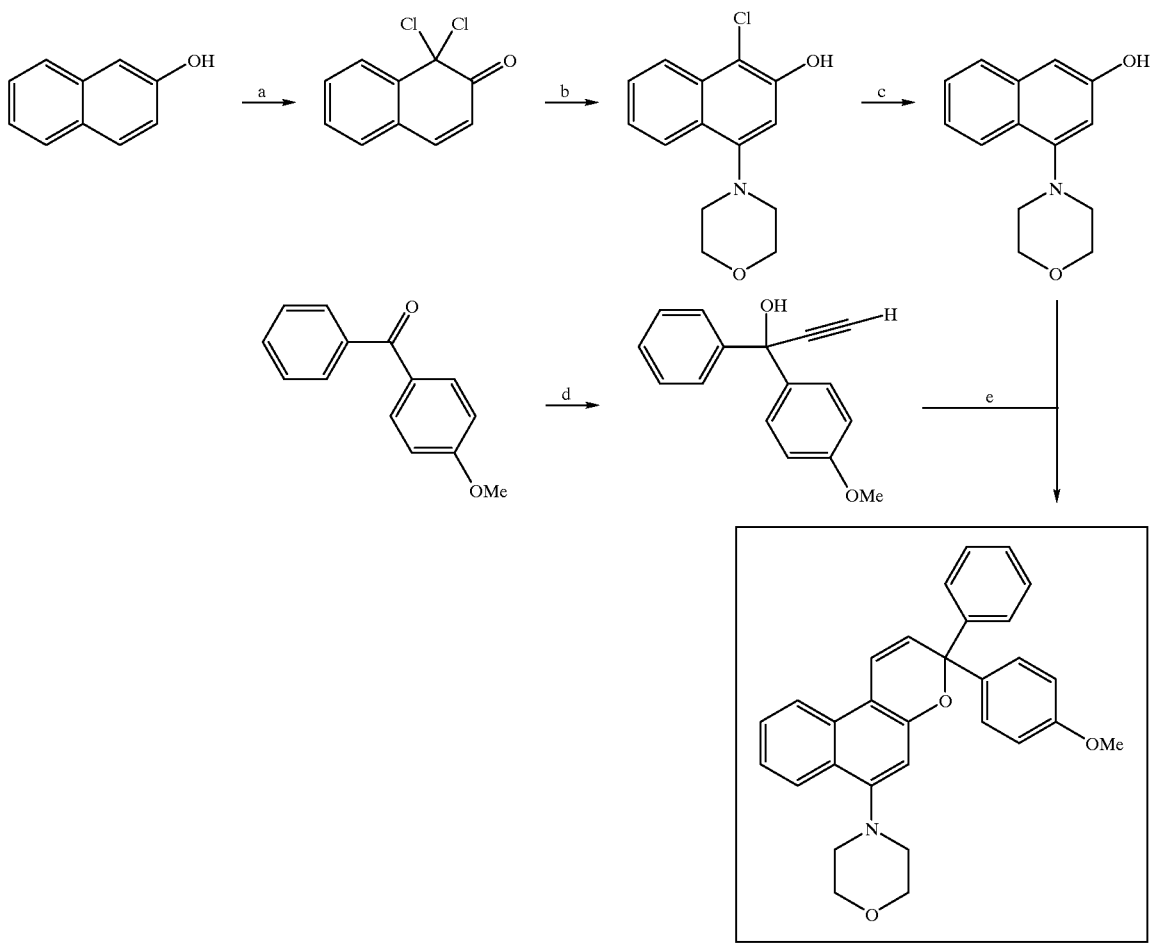

The synthetic route used is essentially that described in the application WO-A-94 22850.

Step (a): 101 g of chlorine gas are allowed to react with 100 g of 2-naphthol in 560 ml of acetic acid in the presence of 280 g of sodium acetate according to the experimental protocol described in J. Chem. Soc. 1945, p 280. 144 g of 1,1-dichloronaphtalene-2(1H)-one are obtained.

Step (b): A mixture constituted of 17.9 g of morpholine and 20.8 g of triethylamine is run into a solution containing 40 g of 1,1-dichloronaphtalene-2(1H)-one in 320 ml of toluene at ambient temperature. After 1.5 hours, the mixture is poured into 200 ml of water. The organic phase is recovered and 300 ml of water followed by a concentrated solution of sodium hydroxide (50 ml) are added. The aqueous phase is recovered and the sodium hydroxide is neutralized by acetic acid which brings about the precipitation of the 1-chloro-4-morpholino-2-naphthol. After filtration, washing with water and drying, 42 g of product are obtained.

Step (c): in a 0.3 l steel autoclave, 10.5 g of 1-chloro-4-morpholino-2-naphthol in 150 ml of sodium hydroxide (2N) and 30 ml of ethanol are maintained under a pressure of 3 bar and at 35° C. in the presence of 3 g of palladium on charcoal (5%) for 7 hours. The solution is then filtered to remove the catalyst. The aqueous phase is then acidified with acetic acid and then filtered. The precipitate is washed with water and then dried. 7.1 g of 4-morpholino-2-naphthol are thus obtained.

Step (d): 1-(p-methoxyphenyl)-1-phenyl-2-propyn-1-ol is synthesized from 4-methoxybenzophenone and lithium acetylide (ethylene diamine complex) in DMSO as described in the patent EP-A-250 193.

Step (e): 0.91 g of 1-chloro-4-morpholino-2-naphthol are allowed to react with 0.95 g of 1-(p-methoxyphenyl)-1-phenyl-2-propyn-1-ol in 30 ml of THF under reflux for 4 hours in the presence of 0.72 g of p-toluene sulfonic acid. The solution is then neutralized with 30 ml of 1N sodium hydroxide and then extracted twice with 30 ml of toluene. The organic phases are evaporated and then the photochrome is separated by chromatography on an alumina column in eluting with a mixture of ethyl acetate/diisopropyl ether (10/90). 250 mg of 3-(p-methoxyphenyl)-3-phenyl-6-morpholino-[3H]-naphtho-[2,1-b]pyran (compound II) are thus obtained. Its structure is confirmed by $^1$H NMR spectroscopy.

EXAMPLE 3

Synthesis of Control Compounds (Compounds Du Type (II))

Compounds C1 to C3 were obtained in a manner analogous to that described above for compound (II).

Structures of compounds (I), (II), C1, C2 and C3

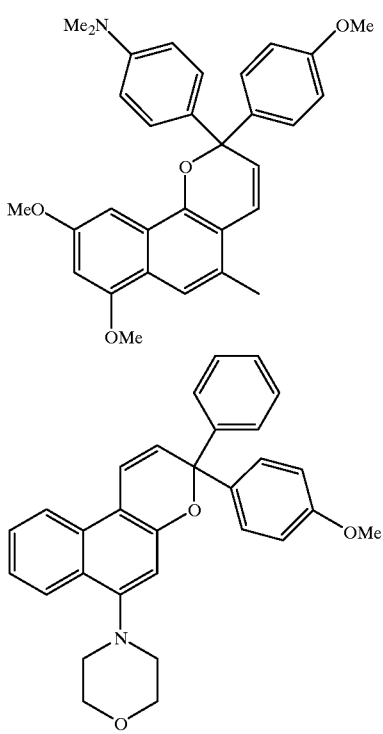

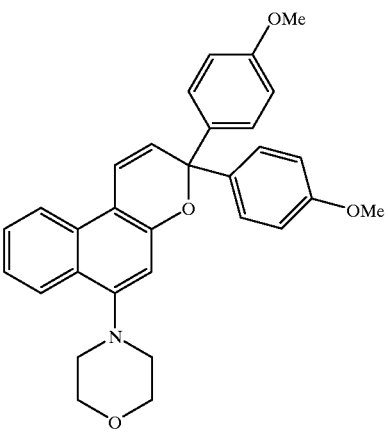

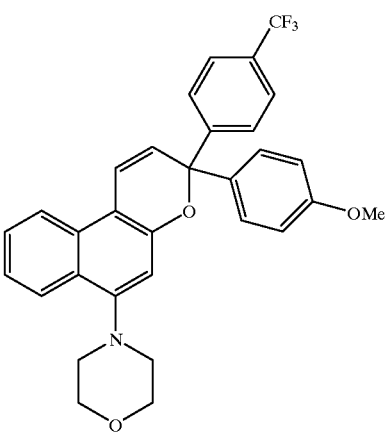

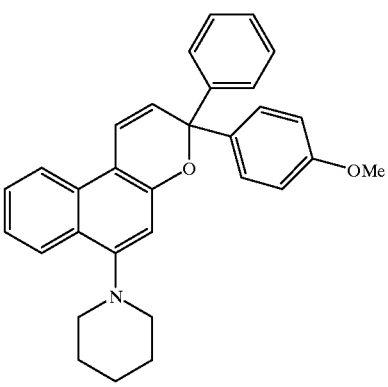

The half-time of fading: $t_{1/2}$, expressed in seconds is specified below for each one of the compounds. This parameter characterizes the kinetics of the return to the initial state (after darkening)(see its exact definition given earlier in the present text with reference to the Table grouping the properties of compound (I)).

| | |
|---|---|
| Compound (I) | 127 s |
| Compound (II) | 88 s |
| Compound C1 | 52 s |
| Compound C2 | 150 s |
| Compound C3 | 165 s |

The interest of compound (II) over certain of its homologues (C2 and C3) is totally obvious.

EXAMPLE 4

Preparation of the Photochromic Matrix

Step 1: Synthesis of the alkenic difunctional monomer of formula (B):

500 g of polyethyleneglycol 600 (Aldrich) are heated at 45° C. in a thermostated reactor under a current of nitrogen. 2.5 g of 4-methoxyphenol (Aldrich) and 3 g of tin dibutyldilaurate (Aldrich) are added into the reactor. 329 g of m-isopropenyl-α-α-dimethylbenzyl isocyanate (m-TMI®) from CYTEC Industries are then added into the reactor at a rate of about 300 g/hour. Once the addition of m-TMI® is complete, the mixture is allowed to stir at 50° C. for one hour. The product obtained is then brought to ambient temperature.

Step 2: Preparation of the (co)polymer: mixture of (meth)acrylate difunctional monomer of formula (A) and alkenic difunctional monomer of formula (B).

21 g of urethane monomer of the preceding step are mixed with 20.5 g of divinylbenzene (Aldrich), 14 g of benzylmethacrylate (Aldrich) and 44.5 g of tetraethoxy Bisphenol A dimethacrylate (DIACRYL 121—AKZO).

Step 3 : Preparation of the matrix: addition of photochromic coloring agents (combination of the two coloring agents) and polymerization conditions:

To the mixture of monomers are added the photochromic coloring agents at the rates given in the following Table (the amounts of the coloring agents are expressed in grams per 100 g of mixture of monomers).

| Sample | Compound (I) | Compound (II) | C1 | C2 | C3 |
|--------|--------------|---------------|-------|--------|-------|
| No 1   | 0.075        | 0.009         | 0     | 0      | 0     |
| No 2   | 0.075        | 0             | 0.015 | 0      | 0     |
| No 3   | 0.075        | 0             | 0     | 0.0075 | 0     |
| No 4   | 0.075        | 0             | 0     | 0      | 0.006 |

0.2 g (by mass) of AMBN 2,2'-azobis(2-methylbutyronitrile) supplied by AKZO (Perkadox®) are dissolved in each composition.

The 2 mm plane samples are then molded between 2 glass plates with a PVC joint. The polymerization is carried out at 60° C. for 8 hours and then at 90° C. for 2 hours. After processing, the samples are re-baked for 1 hour at 120° C.

EXAMPLE 5

Results

The optical transmission between 190 and 900 nm is measured for each sample in the light state (T0) and then in the dark state (TD15) after 15 minutes exposure to UV-visible under a filtered Xenon source (distribution near to AM2 Moon). From the transmission spectra, the chromatic co-ordinates X, Y, Z and L, a, b were calculated according to the ASTM E308-90 method. The yellow index in the light state was calculated from these co-ordinates according to the ASTM D1925-70 method. The photochromic properties of the samples are given in the following Tables.

| Sample | *T0   | **TD15 (25° C.) | **TD15 (40° C.) |
|--------|-------|-----------------|-----------------|
| No 1   | 82.6% | 10.7%           | 34.4%           |
| No 2   | 84.4% | 13.8%           | 37.7%           |
| No 3   | 82.8% | 10.8%           | 33.4%           |
| No 4   | 83.1% | 11.4%           | 32.9%           |

*T0 = transmission measured at 560 nm in the light state
**TD15 = transmission measured at 560 nm after 15 minutes' exposure.

| Sample | Yellow index | a d15 25° C. | b d15 25° C. | a d15 40° C. | b d15 40° C. | Δa $a_{25} - a_{40}$ | Δb $b_{25} - b_{40}$ |
|--------|--------------|--------------|--------------|--------------|--------------|----------------------|----------------------|
| No 1   | 9.8          | 0.2          | −6.8         | −0.6         | −0.8         | 0.8                  | −6.0                 |
| No 2   | 12.7         | 4.0          | −2.8         | 2.0          | 1.4          | 2.0                  | −4.2                 |
| No 3   | 9.9          | 0.6          | −10.3        | −0.7         | −3.6         | 1.3                  | −6.7                 |
| No 4   | 10.6         | 4.0          | −9.6         | −0.8         | −2.1         | 1.8                  | −7.5                 | a d15 and b d15 designate the chromatic co-ordinates in the darkened state after 15 minutes' exposure. Δa and Δb represent the variations in color between 25 and 40° C.

It is demonstrated by these measurements that Sample No. 2 has a yellow index which is too high and a colorability (TD15) at 40° C. which is much lower than the other examples. The colors in the darkened state of this example are not constant: a purple tendency at 25° C. and brown at 40° C.

In the darkened state, Samples No. 3 and 4 are gray with a purple hint at 25° C. and gray with a hint of blue at 40° C. Sample No. 1 with a lower yellow index is gray with a hint of blue at 25° C. and neutral gray at 40° C.

In summary, Sample No. 1 is that which had the best color consistency between 25° and 40° C. (the deviations Δa and Δb are lower for this sample) with a high colorability at 40° C. and a relatively low yellow index.

What is claimed is:

1. A photochromic composition comprising:
    2-(p-dimethylaminophenyl)-2-(p-methoxyphenyl)-5-methyl-7,9-dimethoxy-[2H]-naphtho[1,2-b]pyran and
    3-(p-methoxyphenyl)-3-phenyl-6-morpholino-3H-naphtho-[2,1-b]pyran.

2. A photochromic composition according to claim 1, wherein 2-(p-dimethylaminophenyl)-2-(p-methoxyphenyl)-5-methyl-7,9-dimethoxy-[2H]-naphtho[1,2-b]pyran and 3-(p-methoxyphenyl)-3-phenyl-6-morpholino-3H-naphtho-[2,1-b]pyran are present in a weight ratio of between 7 and 10.

3. A photochromic composition according to claim 1, wherein 2-(p-dimethylaminophenyl)-2-(p-methoxyphenyl)-5-methyl-7,9-dimethoxy-[2H]-naphtho[1,2-b]pyran and 3-(p-methoxyphenyl)-3-phenyl-6-morpholino-3H-naphtho-[2,1-b]pyran are present in a weight ratio of between 8 and 9.

4. A method of making a photochromic polymer matrix, said method comprising:
    disposing 2-(p-dimethylaminophenyl)-2-(p-methoxyphenyl)-5-methyl-7,9-dimethoxy-[2H]-naphtho[1,2-b]pyran and 3-(p-methoxyphenyl)-3-phenyl-6-morpholino-3H-naphtho-[2,1-b]pyran within or on the polymer matrix.

5. A method according to claim 4, wherein 2-(p-dimethylaminophenyl)-2-(p-methoxyphenyl)-5-methyl-7,9-dimethoxy-[2H]-naphtho[1,2-b]pyran and 3-(p-methoxyphenyl)-3-phenyl-6-morpholino-3H-naphtho-[2,1-b]pyran are present in a weight ratio of between 7 and 10.

6. (Co)polymer matrix comprising 2-(p-dimethylaminophenyl)-2-(p-methoxyphenyl)-5-methyl-7,9-dimethoxy-[2H]-naphtho-[1,2-b]pyran, 3-(p-methoxyphenyl)-3-phenyl-6-morpholino-3H-naphtho-[2,1-b]pyran, or combinations thereof.

7. (Co)polymer matrix according to claim 6, wherein the (copolymer is selected from the group consisting of:
   a) optionally halogenated alkyl, cycloalkyl, aryl or aralkyl mono-, di-, tri- or tetraacrylate or mono-, di-, tri- or tetramethacrylate or having at least one ether and/or ester and/or carbonate and/or carbamate and/or thiocarbamate and/or urea and/or amide group,
   b) polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymer, cellulose acetate, tricellulose acetate, cellulose acetate-propionate, or polyvinylbutyral,
   c) copolymers of two or more types of monomer or mixtures of polymers mentioned above,
   d) copolymers obtained by radical polymerization of a composition comprising a mixture of at least one or more difunctional monomers of type (a) and one or more difunctional monomers of type (b):
   the difunctional monomer(s) of type (a) having one or the other of the formulae (A) and (A') below:
   +formula (A):

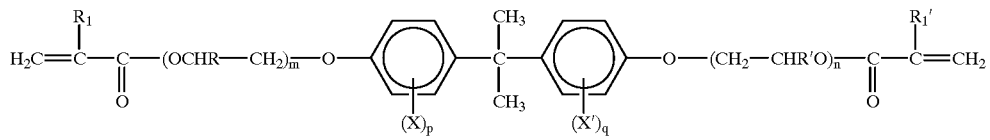

in which:
$R_1$, $R'_1$, R and R', identical or different, independently are a hydrogen or a methyl group;
m and n are, independently, integers between 0 and 4 inclusive;
X and X', identical or different, are a halogen;
p and q are, independently, integers between 0 and 4 inclusive;
formula (A'):

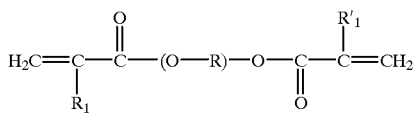

in which:
$R_1$ and $R'_1$, identical or different, independently are a hydrogen or a methyl group;

R is a linear or branched alkyl radical having from 2 to 8 carbon atoms, a cycloalkyl radical having from 3 to 6 carbon atoms, an ether radical of formula (R'—O—R") in which R' and R", identical or different, independently are a linear or branched alkyl radical having from 2 to 4 carbon atoms;
the difunctional monomer(s) of type (b), long chain alkenic difunctional oligomer(s), being of one or the other of formulae (B), (B') and (B") below:
formula (B):

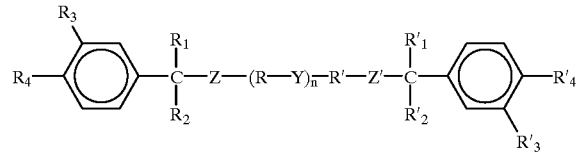

in which:
$R_1$, $R'_1$, $R_2$ and $R'_2$, identical or different, independently are hydrogen or a linear or branched alkyl radical;
$R_3$ and $R_4$, different, are independently one hydrogen and the other an alkenyl radical having from 2 to 6 carbon atoms;
$R'_3$ and $R'_4$, different, are independently one hydrogen and the other an alkenyl radical having from 2 to 6 carbon atoms;

Z represents a carbamate function (—NH—CO—O—), a thiocarbamate function (—NH—CO—S—) or a urea function (—NH—CO—NH—);

Z', independent from Z, represents a carbamate function (—O—CO—NH—), a thiocarbamate function (—S—CO—NH—) or a urea function (—NH—CO—NH—);

R' represents a linear or branched alkyl radical having from 2 to 4 carbon atoms;

R, identical or different when $n \geq 2$, is a linear or branched alkyl radical having from 2 to 4 carbon atoms;

Y, identical or different when $n \geq 2$, is oxygen or sulfur;

n is an integer defined in such a way that the total number of carbon atoms contained in the long chain situated between the two motifs Z and Z' is at least equal to 18;
formula (B'):

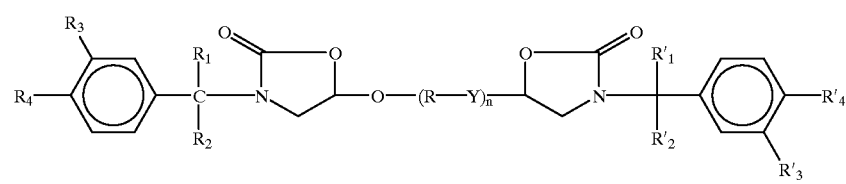

in which:

$R_1$, $R_2$, $R_3$, $R_4$, $R'_1$, $R'_2$, $R'_3$, $R'_4$, R and Y are such as defined above with reference to formula (B);

n is an integer defined in such a way that the total number of carbon atoms contained in the long chain of the motif $(R—Y)_n$ is at least equal to 22;

formula (B"):

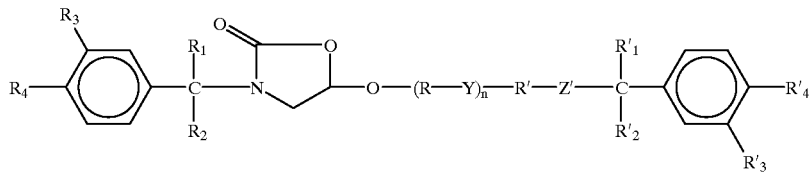

in which:

$R_1$, $R_2$, $R_3$, $R_4$, $R'_1$, $R'_2$, $R'_3$, $R'_4$, R, R' and Y are such as defined above with reference to formula (B);

Z' is a carbamate function (—O—CO—NH—) or Z' is a thiocarbamate function (—S—CO—NH—);

n is an integer defined in such a way that the total number of carbon atoms contained in the long chain of the motif $(R—Y)_n$—R' is at least equal to 22, and e) combinations thereof.

8. (Co)polymer matrix according to claim 7, characterized in that the copolymer is obtained by radical polymerization of a composition defined in point d) and wherein the difunctional monomer(s) of type (a) have formula (A) where:

$R_1$ and $R'_1$, identical, are a methyl group;

R and R', identical, are hydrogen or a methyl group;

m and n, independently, are 1 or 2;

p and q are identical and equal to 0;

and/or wherein, in the long-chain alkenic difunctional oligomer(s) of formula (B) and/or of formula (B') and/or of formula (B"), $R_1$, $R'_1$, $R_2$, and $R'_2$ are identical and represent a methyl group; $R_3$ and $R'_3$ are identical and represent an isopropenyl group; and $R_4$ and $R'_4$ are identical and are hydrogen.

9. (Co)polymer matrix according to claim 7, characterized in that the copolymer is obtained by radical polymerization of a composition defined in point d) of claim 7, wherein, in the alkenic difunctional oligomer(s) of formula (B) and/or of formula (B') and/or of formula (B"), the long polyoxyalkylene and/or polymercaptoalkylene chain, represented by the motif $(R—Y)_n$—R' in the case of oligomer(s) of formula (B) or of formula (B") or by the motif $(R—Y)_n$ in the case of oligomer(s) of formula (B'), has a molecular mass between 500 g.mol$^{-1}$ and 2,000 g.mol$^{-1}$.

10. (Co)polymer matrix according to claim 7, wherein the copolymer is obtained by radical polymerization of a composition defined in point d) of claim 7 and wherein the difunctional oligomer(s) of type (b) have formula (B) in which:

Z and Z' are urea functions (—NH—CO—NH—);

$R_1$, $R'_1$, $R_2$, and $R'_2$ are identical and represent a methyl group; $R_3$ and $R'_3$ are identical and represent an isopropenyl group; and $R_4$ and $R'_4$ are identical and are hydrogen;

R represents an ethylene or propylene group; and n is an integer equal to 13 or 19 which defines a total number of carbon atoms, between Z and Z', equal to 28 or 40 when $(R—Y)_n$ is polyoxyethylene chain; or n is an integer equal to 10 or 14 which defines a total number of carbon atoms, between Z and Z', equal to 33 or 45 when $(R—Y)_n$ is a polyoxypropylene chain; or n is an integer between the lower limits (n is between 10 and 13 inclusive) and higher limit values (n is between 14 and 19 inclusive), when $(R—Y)_n$ is a mixed polyoxyethylene/polyoxypropylene chain, or in which:

Z and Z' are carbamate functions of formula (—NH—CO—O—) and (—O—CO—NH—) respectively;

$R_1$, $R'_1$, $R_2$, and $R'_2$ are identical and represent a methyl group; $R_3$ and $R'_3$ are identical and represent an isopropenyl group; and $R_4$ and $R'_4$ are identical and are hydrogen;

R' represents an ethylene group;

$(R—Y)_n$, represents a long chain polyoxyethylene; and n is an integer equal to 13 or 19 which defines a total number of carbon atoms, contained in the long chain situated between the two motifs Z and Z', equal to 28 or 40.

11. (Co)polymer matrix according to claim 7, wherein the copolymer is obtained by radical polymerization of a composition defined in point d) of claim 7 and wherein the amount of monomer(s) of type (a) is between 40 and 99 parts by weight for 100 parts by weight of the mixture of monomers of type (a) and (b).

12. (Co)polymer matrix according to claim 11, further characterized in that it contains an effective amount of a radical polymerization initiator.

13. (Co)polymer matrix according to claim 12, wherein the radical polymerization initiator is selected from the group consisting of a thermal initiator, a photoinitiator, and a mixture thereof.

14. (Co)polymer matrix according to claim 6, wherein the copolymer matrix comprises a mixture of 2-(p-dimethylaminophenyl)-2-(p-methoxyphenyl)-5-methyl-7,9-dimethoxy-[2H]-naphtho[1,2-b]pyran and 3-(p-methoxyphenyl)-3-phenyl-6-morpholino-3H-naphtho-[2,1-b]pyran.

15. A glazing, optical device, or ophthalmic or solar article comprising a lens, wherein said lens comprises 2-(p-dimethylaminophenyl)-2-(p-methoxyphenyl)-5-methyl-7,9-dimethoxy-[2H]-naphtho[1,2-b]pyran according to claim 4.

16. A glazing, optical device, or ophthalmic or solar article comprising a lens, wherein said lens comprises 3-(p-methoxyphenyl)-3-phenyl-6-morpholino-3H-naphtho-[2,1-b]pyran according to claim 5.

17. A glazing, optical device, or ophthalmic or solar article according to claim 16, wherein said lens further comprises 2-(p-dimethylaminophenyl)-2-(p-methoxyphenyl)-5-methyl-7,9-dimethoxy-[2H]-naphtho[1,2-b]pyran.

18. A glazing, optical device, or ophthalmic or solar article comprising a lens, wherein said lens comprises a matrix according to claim 6.

19. A glazing, optical device, or ophthalmic or solar article comprising a lens, wherein said lens comprises a matrix according to claim 7.

20. A glazing, optical device, or ophthalmic or solar article comprising a lens, wherein said lens comprises a matrix according to claim 8.

21. A glazing, optical device, or ophthalmic or solar article comprising a lens, wherein said lens comprises a matrix according to claim 9.

22. A glazing, optical device, or ophthalmic or solar article comprising a lens, wherein said lens comprises a matrix according to claim 10.

23. A glazing, optical device, or ophthalmic or solar article comprising a lens, wherein said lens comprises a matrix according to claim 11.

24. A glazing, optical device, or ophthalmic or solar article comprising a lens, wherein said lens comprises a matrix according to claim 12.

25. A glazing, optical device, or ophthalmic or solar article comprising a lens, wherein said lens comprises a matrix according to claim 13.

26. A glazing, optical device, or ophthalmic or solar article comprising a lens, wherein said lens comprises a matrix according to claim 14.

27. 2-(p-dimethylaminophenyl)-2-(p-methoxyphenyl)-5-methyl-7,9-dimethoxy-[2H]-naphtho[1,2-b]pyran.

28. 3-(p-methoxyphenyl)-3-phenyl-6-morpholino-3H-naphtho-[2,1-b]pyran.

* * * * *